US00PP31814P2

(12) United States Plant Patent
Rijk

(10) Patent No.: US PP31,814 P2
(45) Date of Patent: May 26, 2020

(54) ***BEGONIA* PLANT NAMED 'DOBEGICPOYEL'**

(50) Latin Name: *Begonia boliviensis*
Varietal Denomination: Dobegicpoyel

(71) Applicant: DUMMEN GROUP B.V., De Lier (NL)

(72) Inventor: Nadine Rijk, De Lier (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/501,712

(22) Filed: May 24, 2019

(51) Int. Cl.
*A01H 5/02* (2018.01)
*A01H 6/18* (2018.01)

(52) U.S. Cl.
USPC ..... Plt./343

(58) Field of Classification Search
USPC ..... Plt./343
CPC ..... A01H 5/02; A01H 6/18
See application file for complete search history.

(56) References Cited

PUBLICATIONS

PLUTO Plant Variety Database Dec. 4, 2019. p. 1.*

* cited by examiner

*Primary Examiner* — Annette H Para
(74) *Attorney, Agent, or Firm* — C. A. Whealy

(57) ABSTRACT

A new and distinct cultivar of *Begonia* plant named 'Dobegicpoyel', characterized by its relatively compact, upright to spreading and mounded plant habit; moderately vigorous growth habit; freely basal branching habit; dark brown-colored leaves; freely and continuously flowering habit; and medium-sized to large double and single flowers that are bright yellow in color.

1 Drawing Sheet

Botanical designation: *Begonia boliviensis.*
Cultivar denomination: 'DOBEGICPOYEL'.

BACKGROUND OF THE INVENTION

The present invention relates to a new and distinct cultivar of *Begonia* plant, botanically known as *Begonia boliviensis*, and hereinafter referred to by the name 'Dobegicpoyel'.

The new *Begonia* plant is a product of a planned breeding program conducted by the Inventor in De Lier, The Netherlands. The objective of the breeding program was to develop new freely branching and flowering *Begonia* plants with large and attractive flowers and tolerance to high temperatures.

The new *Begonia* plant originated from a cross-pollination made by the Inventor of two unidentified selections of *Begonia boliviensis*, not patented. The new *Begonia* plant was discovered and selected by the Inventor as a single flowering plant from within the progeny of the stated cross-pollination in a controlled greenhouse environment in De Lier, The Netherlands in 2008.

Asexual reproduction of the new *Begonia* plant by vegetative tip cuttings in a controlled greenhouse environment in De Lier, The Netherlands since 2008 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'Dobegicpoyel'. These characteristics in combination distinguish 'Dobegicpoyel' as a new and distinct *Begonia* plant:

1. Relatively compact, upright to spreading and mounded plant habit.
2. Moderately vigorous growth habit.
3. Freely basal branching habit.
4. Dark brown-colored leaves.
5. Freely and continuously flowering habit.
6. Medium-sized to large double and single flowers that are bright yellow in color.

Plants of the new *Begonia* can be compared to plants of the parent selections. In side-by-side comparisons, plants of the new *Begonia* differ primarily from plants of the parent selections in growth habit as plants of the new *Begonia* are more uniform than plants of the parent selections.

Plants of the new *Begonia* can be compared to plants of *Begonia boliviensis* 'Beauvilia White', not patented. In side-by-side comparisons, plants of the new *Begonia* differ primarily from plants of 'Beauvilia White' in the following characteristics:

1. Plants of the new *Begonia* have larger leaves than plants of 'Beauvilia White'.
2. Plants of the new *Begonia* have larger flowers than plants of 'Beauvilia White'.
3. Flowers of plants of the new *Begonia* face more upright and outwardly than and not as downward as flowers of plants of 'Beauvilia White'.

BRIEF DESCRIPTION OF THE PHOTOGRAPH

The accompanying colored photograph illustrates the overall appearance of the new *Begonia* plant showing the colors as true as it is reasonably possible to obtain in colored reproductions of this type. Colors in the photograph may differ slightly from the color values cited in the detailed botanical description which accurately describe the colors of the new *Begonia* plant. The photograph is a side perspective view of a typical flowering plant of 'Dobegicpoyel' grown in a container.

DETAILED BOTANICAL DESCRIPTION

Plants used for the aforementioned photograph and following observations and measurements were grown in 12-cm containers during the summer in a glass-covered greenhouse in De Lier, The Netherlands. During the production of the plants, day temperatures ranged from 17° C. to 30° C., night temperatures ranged from 10° C. to 20° C. and minium light level was 135 watt/m$^2$. Plants were ten weeks old when the photograph and the description were taken. In the following description, color references are made to The Royal Horticultural Society Colour Chart, 2015 Edition, except where general terms of ordinary dictionary significance are used.

Botanical classification: *Begonia boliviensis* 'Dobegicpoyel'.

Parentage:

*Female, or seed, parent*.—Unidentified selection of *Begonia boliviensis*, not patented.

*Male, or pollen, parent*.—Unidentified selection of *Begonia boliviensis*, not patented.

Propagation:

*Type*.—By vegetative tip cuttings.

*Time to initiate roots, summer*.—About 18 days at temperatures about 22° C. to 30° C.

*Time to initiate roots, winter*.—About 21 days at temperatures about 22° C. to 30° C.

*Time to produce a rooted young plant, summer*.—About 25 days at temperatures about 22° C. to 30° C.

*Time to produce a rooted young plant, winter*.—About 28 days at temperatures about 20° C. to 25° C.

*Root description*.—Medium in thickness, fibrous; whitish grey in color, actual color of the roots is dependent on substrate composition, water quality, fertilizer type and formulation, substrate temperature and physiological age of roots; plants of the new *Begonia* have not been observed to form tubers.

*Rooting habit*.—Moderately freely branching; medium density.

Plant description:

*Plant form and growth habit*.—Upright to spreading and mounded plant habit; relatively compact; becoming more pendulous with development; freely basal branching with about four lateral branches; moderately vigorous growth habit; moderate growth rate.

*Plant height, soil level to top of foliar plane*.—About 20 cm.

*Plant height, soil level to top of floral plane*.—About 23 cm.

*Plant width*.—About 33 cm by 36 cm.

*Lateral branch description*.—Length: About 14 cm. Diameter: About 1.2 cm. Internode length: About 2.5 cm. Texture and luster: Pubescent; somewhat glossy. Strength: Moderately strong, flexible. Color: Close to 152A; at the internodes, close to 147B.

*Leaf description*.—Arrangement: Alternate, simple. Length: About 19.4 cm. Width: About 8.3 cm. Shape: Ovate to lanceolate. Apex: Narrowly acute. Base: Cordate. Margin: Serrate. Texture and luster, upper surface: Pubescent; somewhat glossy. Texture and luster, lower surface: Pubescent; matte. Venation pattern: Palmate; reticulate. Color: Developing leaves, upper surface: Close to N186A. Developing leaves, lower surface: Close to 59A. Fully expanded leaves, upper surface: Close to 200A; venation, close to 137A. Fully expanded leaves, lower surface: Close to 186A; venation, close to 166A. Petioles: Length: About 8.2 cm. Diameter: About 5 mm. Texture and luster, upper and lower surfaces: Smooth, glabrous; somewhat glossy. Strength: Moderately strong; flexible. Color, upper surface: Close to N144A, becoming closer to 59A with development. Color, lower surface: Close to 152B.

Flower description:

*Flowering habit*.—Medium-sized to large double and single flowers arranged in axillary cymes; freely flowering habit with numerous flowers developing per plant, about 26 open flowers and flower buds per plant at one time; flowers pendulous and face mostly outwardly to somewhat downwardly.

*Fragrance*.—None detected.

*Natural flowering season*.—Plants begin flowering about eight weeks after planting; long flowering period, in the garden plants flower freely and continuously throughout the summer in Northern Europe and can be flowered year-round in greenhouses.

*Flower longevity*.—Individual flowers last about four weeks on the plant; flowers persistent.

*Inflorescence height*.—About 5 cm.

*Inflorescence diameter*.—About 10.5 cm.

*Flower buds*.—Length: About 6 mm. Diameter: About 6 mm. Shape: Ovoid. Texture and luster: Smooth, glabrous; matte. Color: Close to 145A.

*Flower size*.—Diameter: About 5.5 cm by 5.8 cm. Depth (height): About 1.8 cm.

*Flower tepals*.—Quantity per flower and arrangement: Typically five per flower arranged in a single whorl. Length: About 3 cm. Width: About 2.5 cm. Shape: Obovate. Apex: Rounded. Base: Cordate. Margin: Entire. Texture and luster, upper and lower surfaces: Smooth, glabrous; matte. Color: When opening, upper surface: Close to 7A. When opening, lower surface: Close to 1C. Fully opened, upper surface: Close to 7A; venation, close to 4A; color becoming closer to 4A with development. Fully opened, lower surface: Close to 8B or close to 8B tinged with close to 37A; venation, close to 4C; color becoming closer to 4C with development.

*Flower tepaloids*.—Quantity per flower and arrangement: Typically one to 20 per flower arranged in about four whorls. Length: About 2.7 cm. Width: About 1.7 cm. Shape: Obcordate. Apex: Retuse. Base: Cuneate. Margin: Entire. Texture and luster, upper and lower surfaces: Smooth, glabrous; matte. Color: When opening and fully opened, upper surface: Close to 7A; venation, close to 4A; color becoming closer to 4A with development. When opening and fully opened, lower surface: Close to 7C; venation, close to 4C; color becoming closer to 4C with development.

*Flower sepals*.—Quantity per flower and arrangement: Typically five per flower arranged in a single whorl. Length: About 1.3 cm. Width: About 1.3 cm. Shape: Obcordate. Apex: Retuse. Base: Cuneate. Margin: Entire. Texture and luster, upper and lower surfaces: Smooth, glabrous; somewhat glossy. Color: When opening and fully opened, upper surface: Close to 144B. When opening and fully opened, lower surface: Close to 144C.

*Flower peduncles*.—Length: About 5.7 cm. Diameter: About 3 mm. Angle: Mostly upright, bending with the weight of the flowers. Strength: Moderately strong. Texture and luster: Smooth, glabrous; somewhat glossy. Color: Close to 146D.

*Flower pedicels*.—Length: About 1.1 cm. Diameter: About 3 mm. Aspect: Mostly upright, bending with the weight of the flower. Strength: Moderately strong. Texture and luster: Smooth, glabrous; somewhat glossy. Color: Close to 154C.

*Reproductive organs*.—Stamens: Quantity of stamens per flower: About 20. Filament length: About 7 mm. Filament color: Close to 13C. Anther length: About 1.5 mm. Anther shape: Oval. Anther color: Close to 13B. Amount of pollen: Moderate. Pollen color: Close to 14C. Pistils: Quantity of pistils per flower: Three. Pistil length: About 7 mm. Style length: About 1 mm. Style color: Close to 13A. Stigma diameter: About 4 mm. Stigma shape: Curled. Stigma color: Close to 13A. Ovary color: Close to 144A. Fruits and seeds: To date, fruit and seed development have not been observed on plants of the new *Begonia*.

Pathogen & pest resistance: To date, resistance to pathogens and pests common to *Begonia* plants has not been observed on plants of the new *Begonia*.

Temperature tolerance: Plants of the new *Begonia* have been observed to tolerate temperatures ranging from about 10° C. to about 35° C.

It is claimed:

1. A new and distinct *Begonia* plant named 'Dobegicpoyel' as illustrated and described.

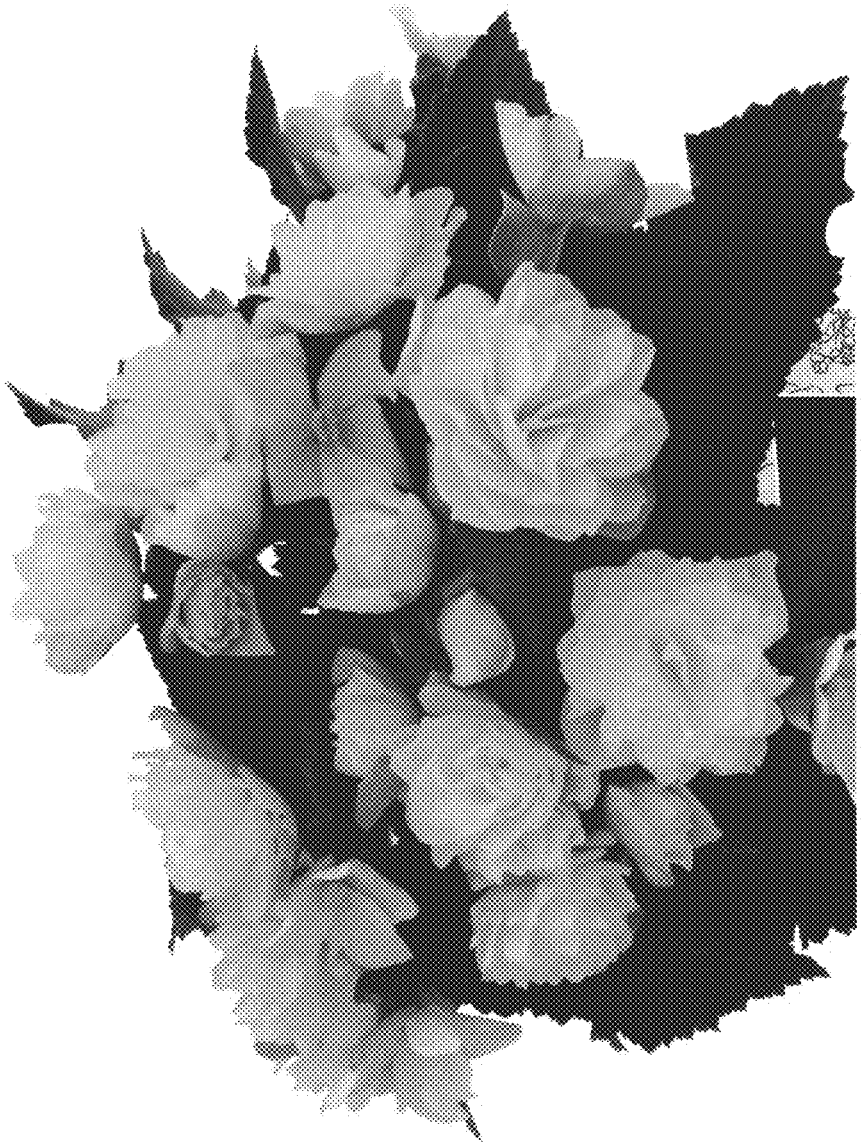

* * * * *